(12) United States Patent
Daniewski et al.

(10) Patent No.: US 6,255,501 B1
(45) Date of Patent: Jul. 3, 2001

(54) PROCESS FOR PREPARING ANTIOSTEOPOROTIC AGENTS

(75) Inventors: Andrzej Robert Daniewski, Bloomfield; Roumen Nikolaev Radinov, Caldwell, both of NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/548,471

(22) Filed: Apr. 13, 2000

Related U.S. Application Data

(60) Provisional application No. 60/130,948, filed on Apr. 26, 1999.

(51) Int. Cl.⁷ .......................... C07D 303/00; C07F 15/00
(52) U.S. Cl. .............................................. 549/545; 556/12
(58) Field of Search ................................ 549/545; 556/12

(56) References Cited

U.S. PATENT DOCUMENTS 8,830,885  * 11/1998 Posner et al. ........................ 514/167

FOREIGN PATENT DOCUMENTS 808 833    11/1997 (EP) .

OTHER PUBLICATIONS

Daniewski A. J. et al, J. Org. Chem. 53, pp 5534–5538 (1998).

* cited by examiner

*Primary Examiner*—Deborah C. Lambkin
*Assistant Examiner*—Andrea M D'Souza
(74) *Attorney, Agent, or Firm*—George W. Johnston; William H. Epstein; John P. Parise

(57) ABSTRACT

Methods for preparing antiosteoportic agents are disclosed. Compounds useful in the methods are also disclosed.

26 Claims, No Drawings

PROCESS FOR PREPARING ANTIOSTEOPOROTIC AGENTS

This application claims benefit of Provisional Application 60/130,948, filed Apr. 26, 1999.

BACKGROUND AND SUMMARY OF THE INVENTION

A vitamin $D_3$ analog III, is currently under evaluation for the treatment of osteoporosis. The existing preparation, described in European Patent Application EP 808833, relies on the Lythgoe phosphine oxide approach, in which CD-ring fragment I is coupled with A-ring fragment II, followed by deprotection of the product to give III.

The present invention provides a process for the preparation of a novel triethylsilyl ether analog of the CD ring fragment, compound 8, as outlined in the following Reaction Scheme.

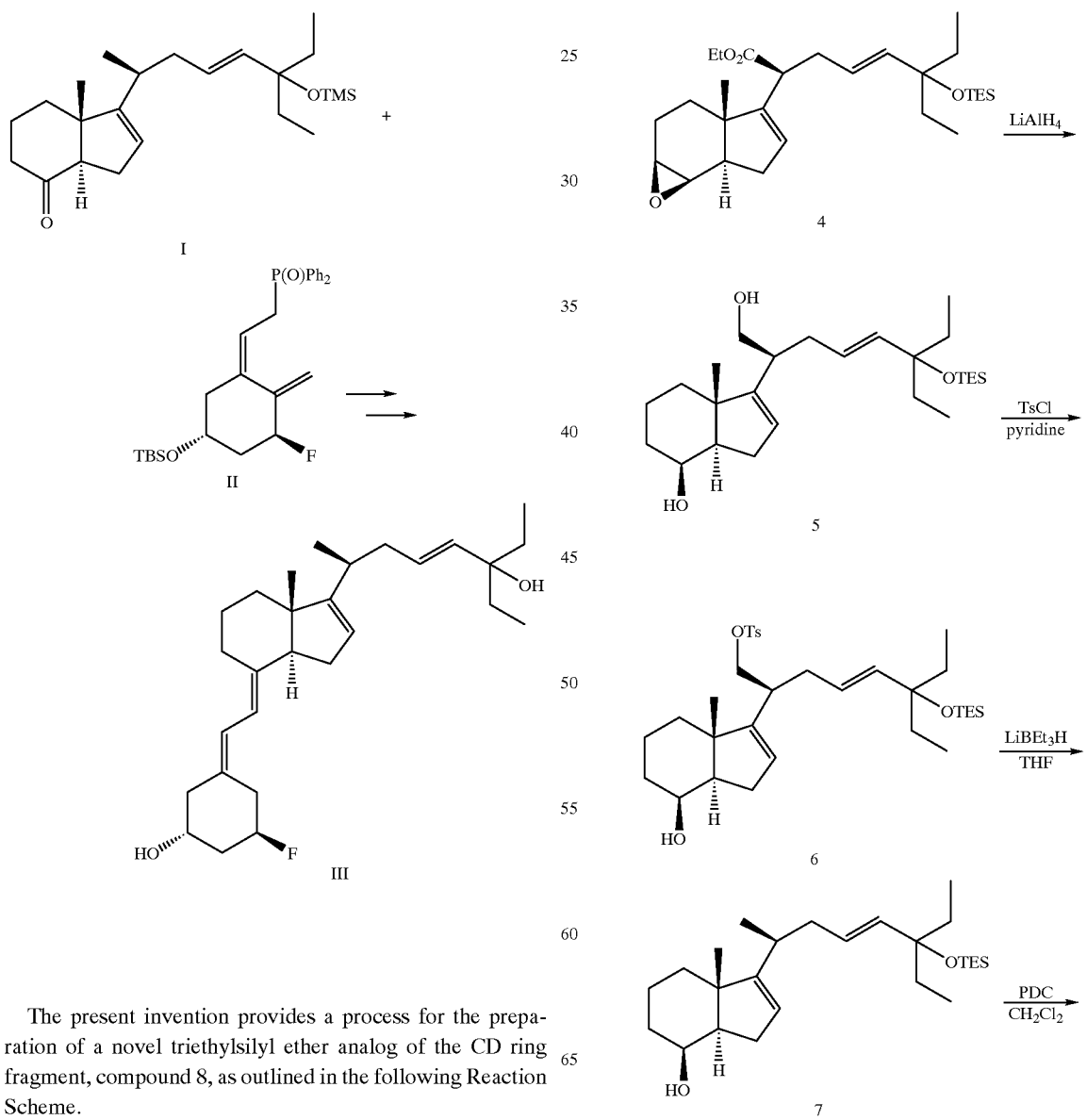

-continued

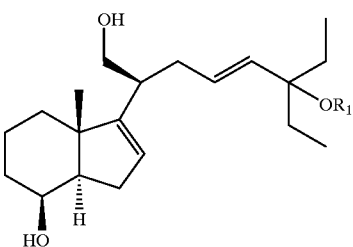

8

Compound 3, used in the above scheme, may be synthesized according to the following scheme:

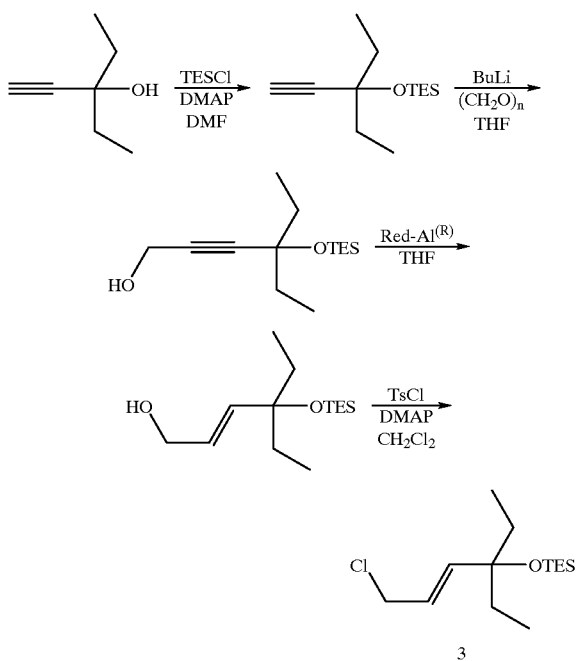

3

The present invention provides a compound having the formula

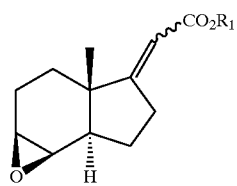

wherein $R_1$ is a lower alkyl group. The present invention also provided a compound having the formula

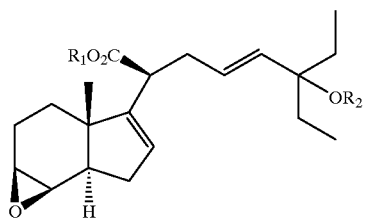

wherein $R_1$ is a lower alkyl group and $R_2$ is a silyl protecting group. The invention further provides a compound having the formula

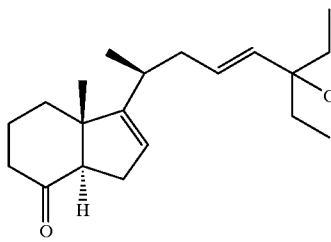

wherein $R_1$ is a silyl protecting group. The invention further provides a compound having the formula

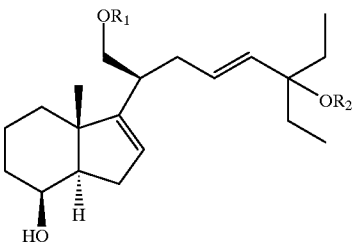

wherein $R_1$ is p-toluenesulfonyl, benzenesulfonyl, methanesulfonyl; and $R_2$ is a silyl protecting group.

The invention also provides a process for producing each of the compounds set forth above.

DETAILED DESCRIPTION OF THE INVENTION

The starting compound 1 is known and may be synthesized in accordance with the procedures set forth in Daniewski, A. R.; Kiegel, J. *J Org. Chem.* 1988, 53, 5534. Compound 1 is converted to an α,β-unsaturated ester 2 (6:1 mixture of E:Z isomers) by a Wittig-Horner reaction under appropriate conditions, leaving the epoxide ring intact. Then, the α,β-unsaturated ester 2 is deprotonated, and the resulting enolate intermediate is alkylated stereoselectively with allylchloride 3, thereby introducing a new chiral center C-20 and the $\Delta^{16}$ double bond (steroid numbering) in the β,γ-unsaturated ester 4. The side chain fragment 3 was obtained in four steps from commercially available 3-ethyl-1-pentyn-3-ol. For the alkylation of α,β-unsaturated ester 2, under optimal conditions, complete deprotonation with minimal decomposition of the substrate was achieved by using lithium dicyclohexylamide (LCA) in the presence of hexamethylphosphoramide (HMPA). The desired (20S)-epimer 4 was obtained in 73% yield by chromatographic separation from the undesired (20R)-epimer (10%). The ester and epoxide functionality in 4 are then reduced simultaneously to yield diol 5. The resulting primary alcohol functionality in 5 is then selectively reduced in two steps to the requisite C-21 methyl group. Oxidation of the product 7 gave the title compound 8. Overall, three intermediates 2, 4, and 7 were chromatographically purified.

In the description of the invention which follows, the term "lower alkyl" is meant to include methyl, ethyl, propyl, butyl. The following terms may be abbreviated: trimethylsilyl (TMS), triethylsilyl (TES), tert-butyldimethyl (TBS), p-toluenesulfonyl (Ts), methanesulfonyl (Ms), dicyclohexylamine (DCHA), butyllithium (BuLi), and hexamethylphosphoramide (HMPA). Other terms may abbreviated as indicated elsewhere in the specification.

The following reagents used in the examples may obtained from the suppliers listed: butyllithium (BuLi), tert-Butyllithium, Chlorotriethylsilane (TESCl), 4-Dimethylaminopyridine (DMAP), Dicyclohexylamine (DCHA), Diisobutylaluminum Hydride (DIBALH), Hexamethylphosphoramide (HMPA), Lithium Aluminum Hydride (LAH), Pyridinium Dichromate (PDC), Red-Al® [Sodium Bis(2-methoxyethoxy)aluminum Hydride], Sodium Ethoxide, and Super-Hydride® (LiBEt$_3$H), from Aldrich Chemical Co.; Triethyl Phosphonoacetate, from Fluka; 3-Ethyl-1-pentyn-3-ol from TCI American; Ruthenium Trichloride Hydrate from Engelhard; Paraformaldehyde from Fluka.

EXAMPLE 1

Preparation of [1aS-(1aα,3aβ,6aα,6bα)]-[octahydro-3a-methyl-2H-indeno[4,5-b]oxiren-4-ylidene]acetic acid, ethyl ester (E/Z mixture of isomers) 2

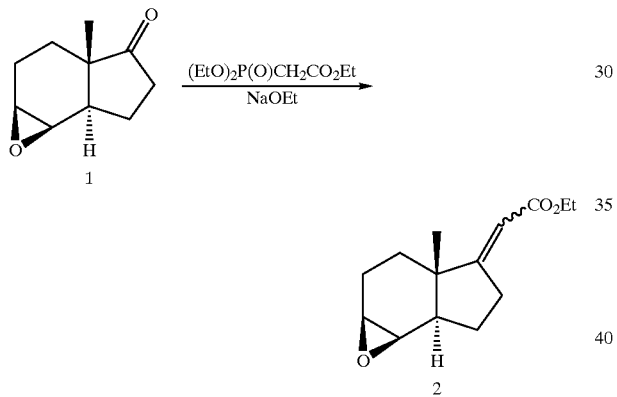

A 250 mL, three-necked, round-bottomed flask equipped with a mechanical stirrer, thermometer and nitrogen bubbler was charged with 87.4 g (390 mmol) of triethyl phosphonoacetate. After warming to 40° C., 26.3 g (387 mmol) of solid sodium ethoxide was added in 5 portions. During the addition, an exotherm ensued that raised the temperature of the reaction mixture to 70° C. After stirring at 46–49° C. (bath temperature, 49° C.) for 1 hour, almost all of the sodium ethoxide dissolved. To the resulting brown solution at 50° C. was added 13.0 g (78.2 mmol) of 1. A mild exotherm ensued that raised the temperature of the reaction mixture to 55° C. The resulting dark brown solution was stirred at 46–49° C. for 2 hour. TLC analysis indicated complete reaction. After cooling to room temperature, the reaction mixture was quenched by the addition of 300 mL of ice-water and the resulting mixture was extracted with 150 mL and again with 100 mL of 8:1 hexane: ethyl acetate. The combined organic layers were concentrated to dryness under reduced pressure, and the residue was dissolved in 200 mL of hexane. The resulting solution was filtered through a pad of TLC silica gel (10 cm in diameter and 3 cm high) and the pad was washed with 100 mL of hexane and 250 mL of 8:1 hexane:ethyl acetate. The combined filtrate and washes were concentrated to dryness under reduced pressure to give 15.4 g of crude 2. This residue was dissolved in 50 mL of pentane and the solution was cooled in a freezer for 30 minutes. The resulting precipitate was collected by filtration, washed with cold pentane to give 7.6 g of the trans-isomer 2. The combined mother liquor and washes were concentrated to dryness under reduced pressure, and the residue was dissolved in 20 mL of pentane and stored in a freezer for 2 hour. This gave 2.7 g of a second fraction of the trans-isomer 2. The combined mother liquor and washes were chromatographed on silica gel to give 3.7 g of 12 as a cis-trans mixture. These three fractions were combined to give a total of 14.0 g of 2 as a mixture of trans:cis isomers.

EXAMPLE 2

Preparation of Epoxy-ester 4

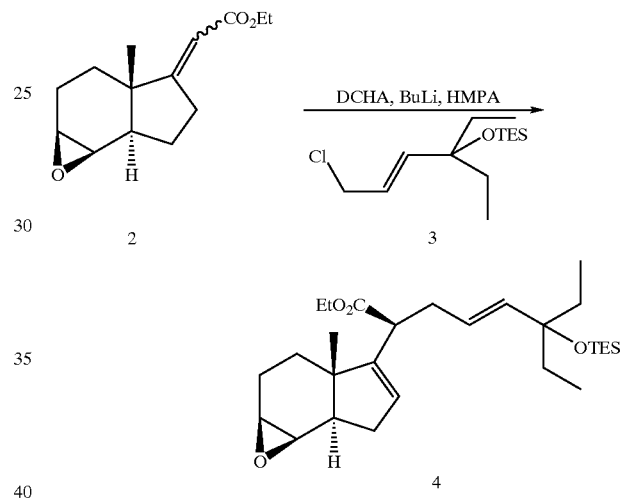

A 250 mL, three-necked, round-bottomed flask equipped with a magnetic stirrer, thermometer and nitrogen bubbler was charged with 10.2 mL (51.4 mmol) of dicyclohexylamine and 46 mL of THF. After cooling with a dry ice-acetone bath to −40° C., 34.6 mL (46.3 mmol) of 1.35M butyllithium in hexanes was added and the mixture was allowed to warm to 0° C.

A separate 500 mL, three-necked, round-bottomed flask equipped with a mechanical stirrer, thermometer, nitrogen bubbler and dropping funnel was charged with 9.45 g (40.0 mmol) of 2, 46 mL of and 128 mL of tetrahydrofuran (THF). After the solution was cooled to −65° C., the solution of lithium dicyclohexylamide prepared above was added slowly, while maintaining the temperature of the reaction mixture between −60 and −65° C. The reaction mixture was stirred at −70° C. for 1 hour, then 14.5 g (52.3 mmol) of 3 was added. The reaction mixture was slowly warmed to −30° C. over 45 minutes. TLC analysis indicated complete reaction. The reaction mixture was quenched by the addition of 20 mL of water, concentrated to a volume of ca. 100 mL and diluted with 150 mL of 8:1 hexane:ethyl acetate, then washed with 2×150 mL=300 mL of water. The combined aqueous washes were back-extracted twice with 100 mL of 8:1 hexane:ethyl acetate, and the organic layers were combined, washed with 50 mL of water, dried over sodium sulfate and concentrated under reduced pressure to dryness. The resulting residue was dissolved in 100 mL of hexane and purified by chromatography on silica gel, eluting with 50:1–20:1 hexane:ethyl acetate. The appropriate fractions were combined and concentrated to give 13.9 g of 4 as a colorless oil.

EXAMPLE 3

Preparation of [3aS-[3(1S*,2E),3aα,7α,7aβ]]-β-[4-ethyl-4-(triethylsilyloxy)-2-hexenyl]-β-[7-hydroxy-3a,4,5,6,7,7a-hexahydro-3a-methyl-1H-inden-3-yl] ethanol 5

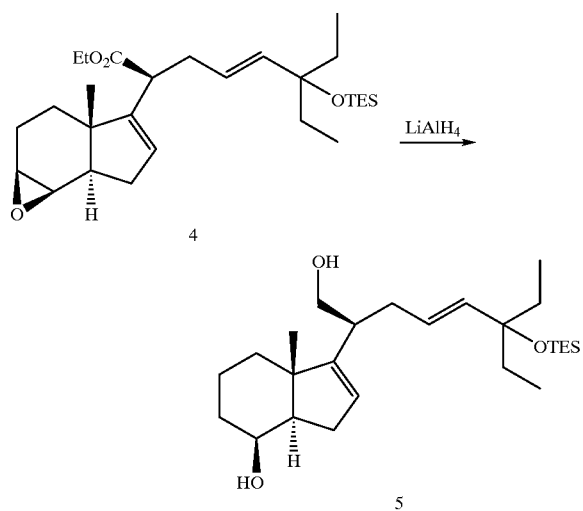

A 500 mL, three-necked, round bottomed flask equipped with a mechanical stirrer, thermometer, addition funnel and nitrogen bubbler was charged with 60 mL (60 mmol) of 1M solution of lithium aluminum hydride in THF. Then, a solution of 16.5 g (34.7 mmol) of 4 in 120 mL of THF was added. An exotherm ensued that raised the temperature of the reaction mixture from 20° C. to 65° C. After stirring at ambient temperature for 1 hour, the reaction mixture was quenched by the careful addition of 20 mL of ethyl acetate, then 20 mL of water was added. After stirring for 0.5 hour, 20 g of sodium sulfate was added and the suspension was stirred for 15 minutes. The solid was removed by filtration through a pad of Celite®, and the pad and collected solids were washed with 100 mL of ethyl acetate. The combined filtrate and washes were concentrated to dryness under reduced pressure to give 16.6 g of crude 5 as a colorless oil. This material was used directly in the next step without further purification.

EXAMPLE 4

Preparation of [3aS-[3(1S*,2E),3aα,7α,7aβ]]-β-[4-ethyl-4-(triethylsilyloxy)-2-hexenyl]-β-[7-hydroxy-3a,4,5,6,7,7a-hexahydro-3a-methyl-1H-inden-3-yl] ethanol4-methylbenezenesulfonic acid ester 6

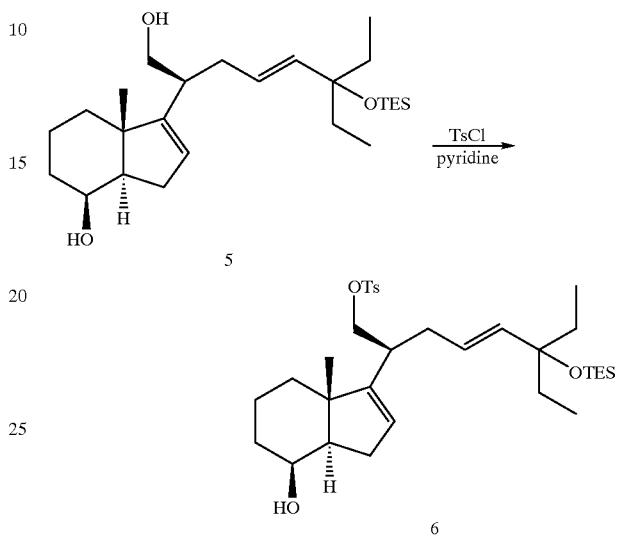

A 500 mL, round-bottomed flask equipped with a magnetic stirrer and nitrogen bubbler was charged with 16.6 g of crude 5 and 100 mL of pyridine. To the resulting solution was added 7.9 g (41.6 mmol) of p-toluenesulfonyl chloride and the mixture was stirred at room temperature for 16 hour. Then, 170 mL of water was added and the mixture was extracted with 200 mL of 4:1 hexane:ethyl acetate. The organic layer was washed twice with 100 mL of water, dried over sodium sulfate and concentrated under reduced pressure, then dried under high vacuum to give 20.6 g of crude 6 as a pale yellow viscous syrup. This material was used directly in the next step without further purification.

EXAMPLE 5

Preparation of [3aS-[3(1S*,3E),3aα,7α,7Aβ]]-3-(5-ethyl-5-(triethylsilyloxy)-1-methyl-3-heptenyl)-3a,4,5,6,7,7a-hexahydro-3a-methyl-1H-inden-7-ol 7

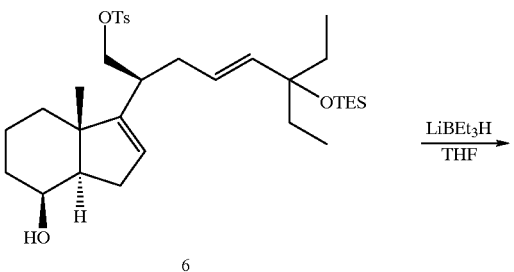

-continued

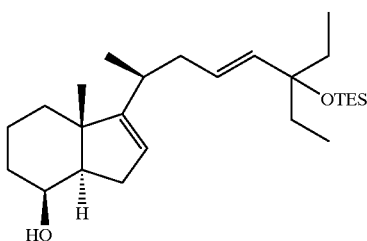

7

A 500 mL, round-bottomed flask equipped with a magnetic stiffer, condenser and nitrogen bubbler was charged with 20.6 g of crude 6 and 70 mL of THF. To the resulting solution was added 139 mL (139 mmol) of 1M solution of Super-Hydrides® in THF. The mixture was heated to reflux for 50 minutes. TLC analysis indicated complete reaction. After cooling to room temperature, the reaction mixture was quenched by the careful addition of 20 mL of methanol, then 200 mL of water was added. The resulting mixture was extracted twice with 100 mL of hexane. The combined organic layers were washed with 100 mL of saturated aqueous potassium bicarbonate solution and concentrated to dryness under reduced pressure. The residue was dissolved in 80 mL of hexane and purified by chromatography on silica gel, eluting with 20:1 hexane:ethyl acetate. The appropriate fractions were combined and concentrated to dryness under reduced pressure to give 11.7 g of 7 as a colorless oil.

EXAMPLE 6

Preparation of [3aR-[1(1S*, 3E),3aα,7aβ]]-1-[5-ethyl-1-methyl-5-[(triethylsilyl)oxy]-3-heptenyl]-3,3a,5,6,7,7a-hexahydro-7a-methyl-4H-inden-4-one 8

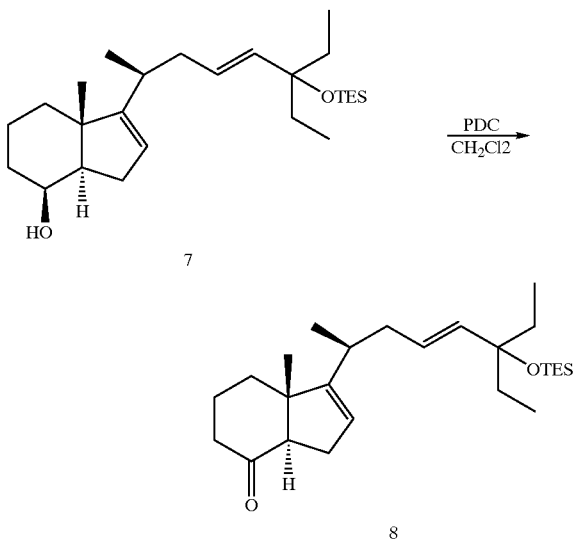

A 100 mL, round-bottomed flask equipped with a magnetic stirrer and nitrogen bubbler was charged with 3.64 g (8.66 mmol) of 7, 40 mL of dichloromethane and 9.04 g (24.0 mmol) of pyridinium dichromate (PDC). The reaction mixture was stirred at room temperature for 16 hour. TLC analysis indicated complete reaction. The reaction mixture was diluted with 80 mL of hexane and filtered through TLC silica gel. The silica gel plug was then washed with 150 mL of 20:1 hexane:ethyl acetate. The combined filtrate and washes were concentrated to dryness under reduced pressure to give 3.1 g (85.6%) of 8 as a colorless oil.

The following procedures set forth the synthesis of the side chain fragment 3.

EXAMPLE 7

Preparation of 3-ethyl-1-pentyn-3-ol TES-ether

A 2 liter, round-bottom flask equipped with a magnetic stirrer and nitrogen bubbler was charged with 67.3 g (300 mmol) of 3-ethyl-1-pentyn-3-ol, 88.2 g (720 mmol) of dimethylaminopyridine (DMAP) and 300 mL of DMF. After cooling to 0–5° C. with an ice bath, 106 mL (640 mmol) of chlorotriethylsilane (TESCl) was added. The cold bath was removed and the mixture was stirred at room temperature for 16 hour. TLC analysis indicated complete reaction. Then, 250 g of ice was added and the mixture was extracted with 500 mL of hexane. The organic layer was washed twice with 200 mL of water and twice with 100 mL of saturated sodium chloride solution, dried over sodium sulfate and concentrated under reduced pressure and ambient temperature to give 149 g of crude 3-ethyl-1-pentyn-3-ol TES-ether as a pale yellow viscous liquid. This material was used directly in the next step without further purification.

EXAMPLE 8

Preparation of 4-ethyl-2-hexyn-1,4-diol TES-ether

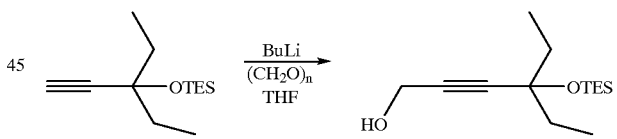

A 2 liter, round-bottom flask equipped with a magnetic stirrer and nitrogen bubbler was charged with 149 g of crude 4-ethyl-2-hexyn-1,4-diol TES-ether and 500 mL of THF After cooling to −70° C. with a dry ice-acetone bath, 360 mL (720 mmol) of 2.0M butyllithium in hexanes was added and the mixture was stirred at −70° C. for 30 minutes. After warming to ambient temperature, the flask was equipped with a reflux condenser and 5.0 g (167 mmol as formaldehyde) of paraformaldehyde was added. After a few minutes an exothermic reaction initiated. When the initial exotherm subsided, a total of 45.0 g (1.45 mol as formaldehyde) of paraformaldehyde was added in 5 g portions, so as to maintain a gentle reflux. The exotherm was easily controlled by the rate of addition of paraformaldehyde and cooling was normally not required. After the solids had dissolved and the exotherm had subsided, the resulting clear yellow solution was heated to reflux for 2 hour, then allowed to cool to room temperature. The reaction mixture was cooled with an ice-water bath, then quenched by the addition of 400 mL of saturated aqueous ammonium chloride solution. The aqueous layer was back-extracted twice with 200 mL of diethyl ether. The combined organic layers were washed twice with 200 mL of saturated sodium chloride solution, dried over sodium sulfate and concentrated to dryness under reduced pressure. The residue was dissolved in 200 mL of 1:9 diethyl ether:hexane and filtered through 200 g of silica gel 60 (230–400 mesh). The silica gel plug was then eluted with 2 liter of 1:9 diethyl ether:hexane. The combined eluates were concentrated under reduced pressure, then under high vacuum to give 168 g of crude 4-ethyl-2-hexyn-1,4-diol TES-ether as a pale yellow viscous liquid. This material was used directly in the next step without further purification.

EXAMPLE 9

Preparation of (E)-4-ethyl-2-hexen-1,4-diol TES-ether

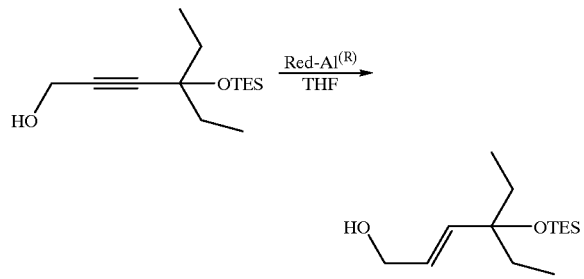

A 3 liter, round-bottom flask equipped with a mechanical stirrer, dropping funnel, thermometer and nitrogen bubbler was charged with 168 g of crude 4-ethyl-2-hexyn-1,4-diol TES-ether and 1 liter of THF. After cooling to −70° C. with a dry ice-acetone bath, 200 mL (600 mmol) 65+wt. % solution of Red-Al® in toluene was added slowly to control vigorous gas evolution and foaming during addition of the first 50% of the reagent. Then, the mixture was warmed to 0° C. with an ice bath and stirred for 1 hour. TLC analysis indicated complete reaction. The mixture was cooled to −70° C. and carefully quenched by the addition of 240 mL of 30% ammonium hydroxide solution, while maintaining the internal temperature below −50° C. The mixture was concentrated under reduced pressure to remove the THF and the resulting slurry was diluted with 400 mL of diethyl ether. The solid was removed by filtration and washed twice with 200 mL of diethyl ether. The combined filtrate and washes were washed twice with 200 mL of water and twice with 200 mL of saturated sodium chloride solution, dried over sodium sulfate and concentrated under reduced pressure, then under high vacuum to give 160 g of crude (E)-4-ethyl-2-hexen-1,4-diol TES-ether as a pale yellow viscous liquid. This material was used directly in the next step without further purification.

EXAMPLE 10

Preparation of Allylic Chloride 3

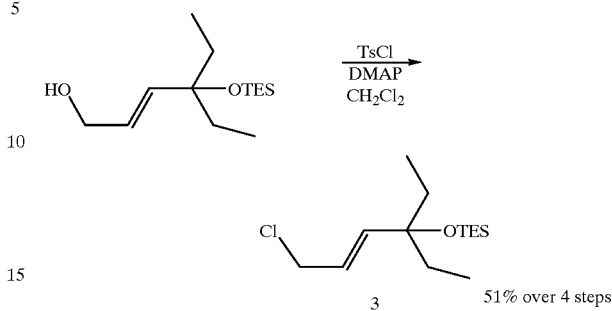

A 2 liter, round-bottom flask equipped with a magnetic stirrer and nitrogen bubbler was charged with 147 g (550 mmol, theoretical) of crude (E)-4-ethyl-2-hexen-1,4-diol TES-ether, 75.0 g (620 mmol) of dimethylaminopyridine (DMAP) and 500 mL of methylene chloride. After cooling to 0° C. with an ice bath, 113 g (600 mmol) of p-toluenesulfonyl chloride (TsCl) was added. The mixture was stirred at 0–5° C. for 30 minutes, and at room temperature for 16 hour, then 1 liter of hexane was added. The resulting precipitate was removed by filtration and washed thoroughly twice with 300 mL of hexane. The combined filtrate and washes were washed consecutively twice with 200 mL of 10% copper sulfate solution, twice with 200 mL of water, twice with 200 mL of saturated sodium bicarbonate solution and twice with 200 mL of saturated sodium chloride solution, dried over sodium sulfate and concentrated to dryness under reduced pressure. The residue was dissolved in 250 mL of hexane and filtered through 750 g of silica gel 60 (230–400 mesh). The silica gel plug was then eluted with 1.25 liter of hexane. The combined eluates were concentrated under reduced pressure and the residue was distilled under high vacuum. A more volatile fraction containing by-products was initially collected, followed by 72.8 g of pure 3 as a colorless liquid.

What is claimed is:

1. A compound having the formula

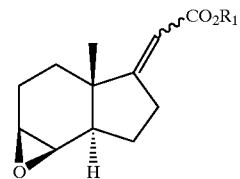

wherein $R_1$ is a lower alkyl group.

2. The compound of claim 1, wherein $R_1$ is methyl.
3. The compound of claim 1, wherein $R_1$ is ethyl.
4. The compound of claim 1, wherein $R_1$ is propyl.
5. The compound of claim 1, wherein $R_1$ is butyl.
6. The compound of claim 1, wherein $R_1$ is tert-butyl.

7. A compound having the formula

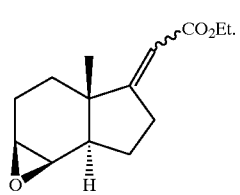
2

8. A compound having the formula

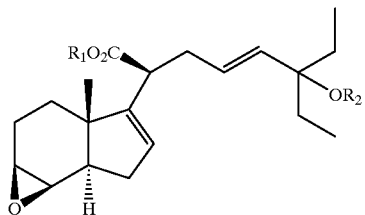

wherein $R_1$ is a lower alkyl group and $R_2$ is a silyl protecting group.

9. The compound of claim 8, wherein $R_1$ is methyl, ethyl, propyl, butyl or tert-butyl; and $R_2$ is trimethylsilyl.

10. The compound of claim 8, wherein $R_1$ is methyl, ethyl, propyl, butyl or tert-butyl; and $R_2$ is triethylsilyl.

11. The compound of claim 8, wherein $R_1$ is methyl, ethyl, propyl, butyl or tert-butyl; and $R_2$ is tert-butyldimethylsilyl.

12. A compound having the formula

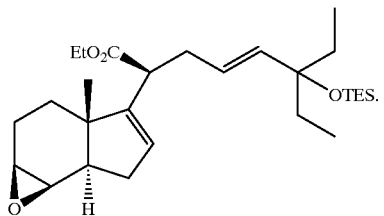
4

13. A compound having the formula

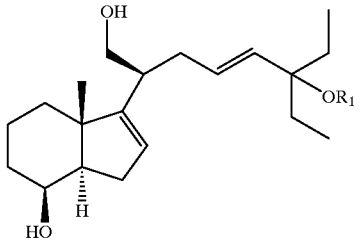

wherein $R_1$ is a silyl protecting group.

14. The compound of claim 13, wherein $R_1$ is trimethylsilyl.

15. The compound of claim 13, wherein $R_1$ is triethylsilyl.

16. The compound of claim 13, wherein $R_1$ is tert-butyldimethylsilyl.

17. A compound having the formula

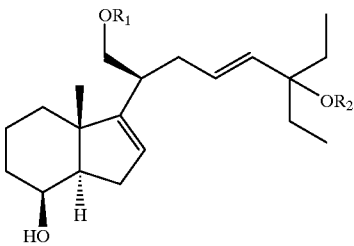

wherein $R_1$ is p-toluenesulfonyl (Ts), benzenesulfonyl, methanesulfonyl and $R_2$ is a silyl protecting group.

18. The compound of claim 17, wherein $R_2$ is trimethylsilyl.

19. The compound of claim 17, wherein $R_2$ is triethylsilyl.

20. The compound of claim 17, wherein $R_2$ is tert-butyldimethylsilyl.

21. A compound having the formula

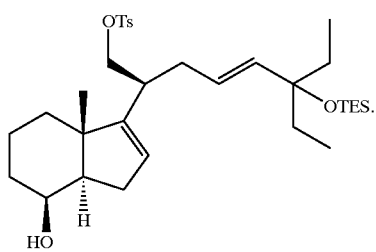
6

22. A process for producing a compound having the formula

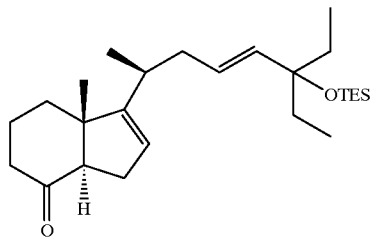
8 comprising i) reacting a compound having the formula

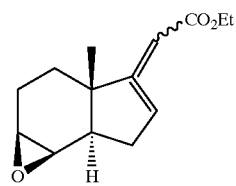
2 with a compound having the formula

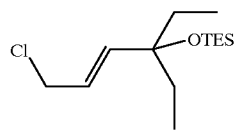
3 in the presence of dicyclohexylamine, butyllithium, and hexamethylphosphoramide to yield a compound having the formula

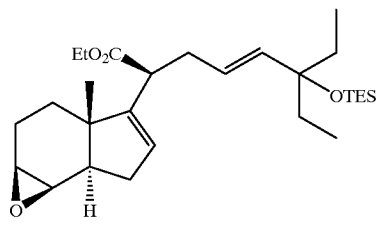
4 ii) reacting compound 4 with LiAlH₄ to produce compound 5 having the formula

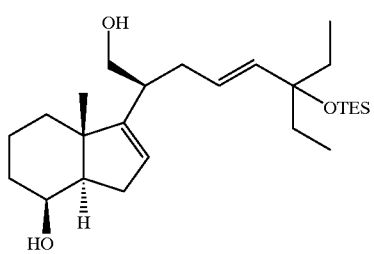
5 iii) reacting the compound 5 with TsCl and pyridine to produce compound 6 having the formula

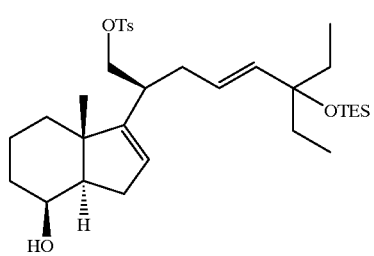
6 iv) reacting compound 6 with LiBEt₃H in the presence of tetrahydrofuran to produce compound 7 having the formula

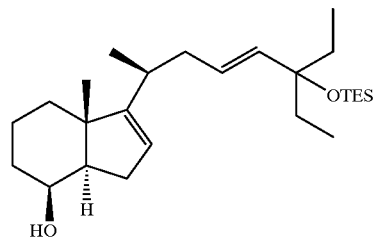
7 v) reacting compound 7 with PDC in the presence of CH₂Cl₂ to produce compound 8.

23. A process for producing a compound having the formula

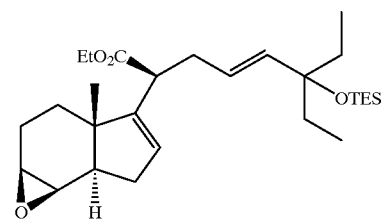
4 comprising reacting a compound having the formula

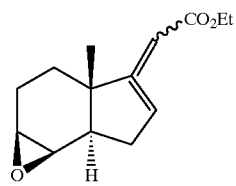
2 with a compound having the formula

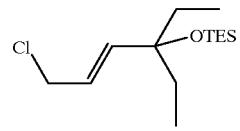
3 in the presence of dicyclohexylamine, BuLi, and hexamethylphosphoramide.

24. A process for producing a compound having the formula

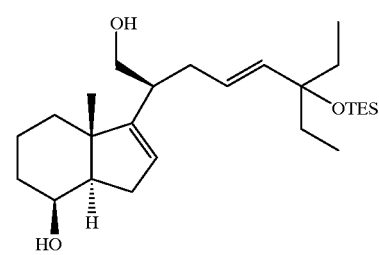
5 comprising reacting compound 4 with LiAlH₄.

25. A process for producing a compound having the formula
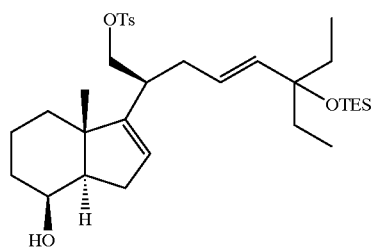
6
comprising reacting the compound 5 with p-toluenesulfonyl chloride and pyridine.
26. A process for producing a compound having the formula
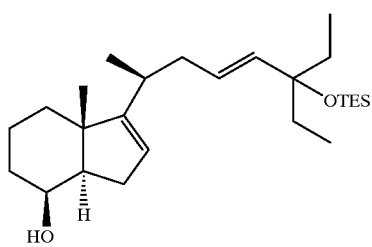
7
comprising reacting the compound 6 with LiBEt$_3$H in the presence of tetrahydrofuran.
* * * * *